(12) United States Patent
Hecht et al.

(10) Patent No.: US 9,192,191 B2
(45) Date of Patent: Nov. 24, 2015

(54) ULTRAVIOLET DISINFECTING DEVICE FOR FOOD AND BEVERAGE DISPENSERS

(75) Inventors: Thomas R. Hecht, Winters, CA (US); Richard A. Martindale, Vacaville, CA (US)

(73) Assignee: Automatic Bar Controls, Inc., Vacaville, CA (US)

( * ) Notice: Subject to any disclaimer, the term of this patent is extended or adjusted under 35 U.S.C. 154(b) by 151 days.

(21) Appl. No.: 13/112,969

(22) Filed: May 20, 2011

(65) Prior Publication Data

US 2011/0286883 A1 Nov. 24, 2011

Related U.S. Application Data

(60) Provisional application No. 61/346,805, filed on May 20, 2010.

(51) Int. Cl.
*A23L 3/28* (2006.01)
*B67D 1/00* (2006.01)
(Continued)

(52) U.S. Cl.
CPC .................. *A23L 3/28* (2013.01); *B67D 1/0086* (2013.01); *A61L 2/10* (2013.01); *A61L 2202/15* (2013.01); *A61L 2202/16* (2013.01); *B67D 2001/075* (2013.01)

(58) Field of Classification Search
CPC ............. A61L 2/00; A61L 2/02; A61L 2/048; A61L 2/10; A61L 2/24; A61L 2202/00; A61L 2202/10; A61L 2202/11; A61L 2202/122; A61L 2202/14; B67D 1/07; B67D 99/00; B67D 2201/00; B67D 2201/00013; B67D 2201/00015; B67D 2201/00081; B67D 2201/00091; B67D 1/0086; G21L 5/08; A23L 3/28

USPC ................ 250/455.11; 422/24, 186.3, 186.07
See application file for complete search history.

(56) References Cited

U.S. PATENT DOCUMENTS

| 6,832,487 B1 | 12/2004 | Baker |
| 7,074,277 B2 | 7/2006 | Tuyls et al. |
| 7,762,431 B1 | 7/2010 | Tuyls et al. |

(Continued)

FOREIGN PATENT DOCUMENTS

WO 2009/098394 A1 8/2009

OTHER PUBLICATIONS

International Search Report and Written Opinion mailed Aug. 17, 2011 in PCT Application No. PCT/US11/37405 filed May 20, 2011.

(Continued)

*Primary Examiner* — Regina M Yoo
(74) *Attorney, Agent, or Firm* — Kilpatrick Townsend & Stockton LLP

(57) ABSTRACT

Disinfecting devices and related methods are provided that apply germicidal ultraviolet light to disinfect dispensing components of food and beverage dispensers. A disinfecting holster for a bar gun includes a support surface configured to interface with a bar gun to support the bar gun when stowed in the holster, a housing coupled with the support surface and surrounding a dispensing nozzle of the bar gun when the bar gun is stowed in the holster, and an ultraviolet light source configured to emit germicidal ultraviolet light onto the nozzle. The housing substantially contains the ultraviolet light within the housing during the application of the ultraviolet light to the dispensing nozzle. The ultraviolet light can be periodically applied to maintain the nozzle in a disinfected state.

10 Claims, 9 Drawing Sheets

(51) Int. Cl.
*A61L 2/10* (2006.01)
*B67D 1/07* (2006.01)

(56) References Cited

U.S. PATENT DOCUMENTS

| | | |
|---|---|---|
| 8,033,430 B2 | 10/2011 | Salmela et al. |
| 2001/0010318 A1 | 8/2001 | Saveliev et al. |
| 2002/0063954 A1 | 5/2002 | Horton, III |
| 2004/0052680 A1 * | 3/2004 | Elwood et al. ................. 422/24 |
| 2004/0155201 A1 * | 8/2004 | Russell et al. ........... 250/455.11 |
| 2007/0137726 A1 | 6/2007 | Yan |
| 2009/0189084 A1 | 7/2009 | Pinsky |
| 2009/0277927 A1 * | 11/2009 | Schroeder et al. ............ 222/108 |
| 2010/0000618 A1 | 1/2010 | Bertucci et al. |

OTHER PUBLICATIONS

Extended European Search Report mailed Feb. 20, 2014, from European Application No. 11784351.6 (7 pages).

* cited by examiner

ULTRAVIOLET DISINFECTING DEVICE FOR FOOD AND BEVERAGE DISPENSERS

CROSS-REFERENCES TO RELATED APPLICATIONS

This application claims the benefit of U.S. Provisional Application No. 61/346,805, entitled "Ultraviolet Disinfecting Device for Food and Beverage Dispensers," filed May 20, 2010, the entire disclosure of which is hereby incorporated herein by reference.

BACKGROUND

The present invention is related to food and beverage dispensers, and more specifically to a method and means to provide ultraviolet disinfection of dispensing points of food and beverage dispensers.

Food and beverage dispensers can become contaminated with molds and/or bacteria. Such molds and/or bacteria can then be inadvertently passed along for consumption, thereby posing a potential health threat. Such contamination can occur in various ways.

For example, FIGS. 1a, 1b, and 1c show a known bar gun 12 (or beverage dispenser) that is placed in its holster 14. Such a bar gun 12 and holster 14 set up is commercially available from the assignee of this patent application. FIG. 1a depicts the general position of the dispensing nozzle 16 of the bar gun 12 as it is being inserted into the holster 14, while being supported by the operator's hand. FIG. 1b depicts the at-rest (or unsupported) position of the bar gun 12 when stowed in the holster 14. The weight of the tubing bundle (not shown) attached to the bar gun 12, along with location of the center of gravity of the bar gun 12 relative to the holster 14, can cause the dispensing nozzle 16 to come into direct contact with the potentially contaminated interior surface 18 of the holster 14. The holster-based solution includes a generally cylindrical member that is configured to accept and encompass the nozzle of the bar gun, and provide a collection device for fluid discharged by the bar gun. This collection device may or may not be fitted with a drainage means, such as the drain line 20 shown. Additionally, while the collection device does provide for collection of fluid discharged from the dispensing nozzle 16 of the bar gun 12, continued use may cause a build-up on the interior surface 18 of the holster 14 as the fluids dry. Furthermore, if not regularly attended to, the interior surface 18 of the collection device can provide a medium for the growth of bacteria and/or molds. The size of the collection device can also readily allow for contact between the dispensing nozzle 16 and the inner surface 18 of the collection device, and thus potentially contaminating the dispensing nozzle through which the next beverage is dispensed to a customer.

Additionally, existing beverage dispensers, for example, hand-held beverage dispensers (e.g., a bar gun), are prone to contamination due to frequent handling by one or more users (who may have less than sanitary hands). Additionally, the residue of fluids dispensed by beverage dispensers often provides an environment that supports the growth of molds and/or bacteria either airborne or deposited by unsanitary contact. Such molds and/or bacteria may then be transferred into a dispensed beverage that is then consumed.

There is therefore a need to provide a way to disinfect food and beverage dispensers to avoid dispensing food and/or beverages that contain pathogens such as molds and/or bacteria.

BRIEF SUMMARY

The present invention provides a method and means to disinfect dispensing components of food and beverage dispensers (e.g., a dispensing port of a food dispenser, a dispensing nozzle of a beverage dispenser). The dispensing components are subjected to contained ultraviolet radiation of adequate duration and intensity to disinfect the dispensing components. Various approaches can be used to trigger the application of the ultraviolet light, such as by triggering the application when a beverage dispenser such as a bar gun is returned to its support, and/or activation at regular intervals (e.g., intervals not exceeding a maximum period of non-activation). To enhance the impact of the applied ultraviolet light, some or all of the dispensing components can be made from materials that can be at least partially penetrated by ultraviolet light (e.g., ultraviolet transparent (UVT) materials) to pass the ultraviolet light onto surfaces potentially in need of disinfection, while being suitable for food contact (e.g., NSF/ANSI Std. 51 materials (National Sanitation Foundation—Food Equipment Materials). The ultraviolet light can also be used to generate ozone for additional germicidal and/or deodorant action. The generated ozone can be applied to the dispensing components to penetrate into areas that the ultraviolet light does not reach.

Thus, in one aspect, a disinfecting holster for a bar gun is provided. The disinfecting holster includes a support surface configured to interface with a bar gun to support the bar gun when stowed in the holster, a housing coupled with the support surface and surrounding a dispensing nozzle of the bar gun when the bar gun is stowed in the holster, and an ultraviolet light source configured to emit germicidal ultraviolet light onto the nozzle. The housing substantially contains the ultraviolet light within the housing.

The disinfecting holster can further include a controller to periodically activate the ultraviolet light source to maintain the nozzle in a disinfected state. The controller can provide for automated and/or manually-initiated applications of ultraviolet light.

The housing can be configured to distribute the ultraviolet light. For example, the housing can include a reflective internal surface configured to reflect the ultraviolet light onto the nozzle. The reflective internal surface can be shaped to distribute the ultraviolet light within the housing.

Ozone can be generated by the ultraviolet light and used to supplement the disinfecting action of the ultraviolet light. For example, a fan can be used to distribute ozone generated by the ultraviolet light within the housing.

In another aspect, a self-disinfecting beverage dispenser is provided. The self-disinfecting beverage dispenser includes a dispensing nozzle, a disinfecting chamber movable to surround the dispensing nozzle, and an ultraviolet light source configured to emit germicidal ultraviolet light to disinfect the dispensing nozzle. The disinfecting chamber substantially contains the ultraviolet light within the disinfecting chamber.

The self-disinfecting beverage dispenser can include additional components. For example, the beverage dispenser can include an actuation mechanism coupled with the disinfecting chamber to move the disinfecting chamber from a first position in which the nozzle is not surrounded by the disinfecting chamber to a second position in which the nozzle is surrounded by the disinfecting chamber. The beverage dispenser can include a controller to control the actuation mechanism and/or to periodically activate the ultraviolet light source to maintain the nozzle in a disinfected state. The controller can provide for automated and/or manually-initiated application of ultraviolet light.

The disinfecting chamber can be configured to distribute the ultraviolet light. For example, the disinfecting chamber can include a reflective internal surface configured to reflect the ultraviolet light onto the nozzle. The reflective internal surface can be shaped to distribute the ultraviolet light within the disinfecting chamber.

Ozone can be generated by the ultraviolet light and used to supplement the disinfecting action of the ultraviolet light. For example, a fan can be used to distribute ozone generated by the ultraviolet light within the disinfecting chamber.

In another aspect, a method is provided for disinfecting a food dispenser. The method includes surrounding a dispensing port of a food dispenser with an enclosure, and emitting germicidal ultraviolet light onto the dispensing port. The enclosure substantially contains the ultraviolet light within the enclosure. The ultraviolet light is emitted during a time period and at an intensity selected to disinfect the dispensing port. The food dispenser can be used to dispense food and/or beverages. For example, the dispensing port can include a fluid dispensing nozzle.

The step of emitting the ultraviolet light onto the dispensing port can include the use of a controller to control an activation of an ultraviolet light source. For example, the controller can be configured to periodically activate the ultraviolet light source to maintain the dispensing port in a disinfected state. The controller can be configured for automated and/or manually-initiated emission of the ultraviolet light.

The step of emitting the ultraviolet light onto the dispensing port can be accomplished in a variety of suitable approaches. For example, a plurality of ultraviolet light sources can be distributed around the enclosure. The ultraviolet light can be reflected from an inner reflective surface of the enclosure to distribute the ultraviolet light within the enclosure.

Ozone can be generated by the ultraviolet light and used to supplement the disinfecting action of the ultraviolet light. For example, a fan can be used to distribute ozone generated by the ultraviolet light within the enclosure.

In another aspect, a retrofit kit is provided for incorporating an ultraviolet light disinfection system onto an existing food or beverage dispenser. The retrofit kit includes an ultraviolet light source configured to couple with an existing food or beverage dispenser and emit germicidal ultraviolet light onto a dispensing port of the dispenser, and a housing configured to couple with the dispenser and surround the dispensing port to contain the emitted ultraviolet light. The retrofit kit can further include a controller to periodically activate the ultraviolet light source to maintain the dispensing port in a disinfected state. Installation hardware can be included in the retrofit kit for coupling the housing and the ultraviolet light source with the dispenser.

For a further understanding of the nature and advantages of the invention, reference should be made to the following description taken in conjunction with the accompanying figures. It is to be expressly understood, however, that each of the figures is provided for the purpose of illustration and description only and is not intended as a definition of the limits of the embodiments of the present invention.

BRIEF DESCRIPTION OF THE DRAWINGS

FIG. 1a shows a known bar gun positioned relative to a cylindrical holster as held by a user during its insertion into the holster.

FIG. 1b shows a typical position of known bar gun relative to a cylindrical holster after it has been released by the user.

FIG. 1c shows a perspective view of the known bar gun and cylindrical holster of FIG. 1a.

DETAILED DESCRIPTION

Figures 1A, 1B, 1C:
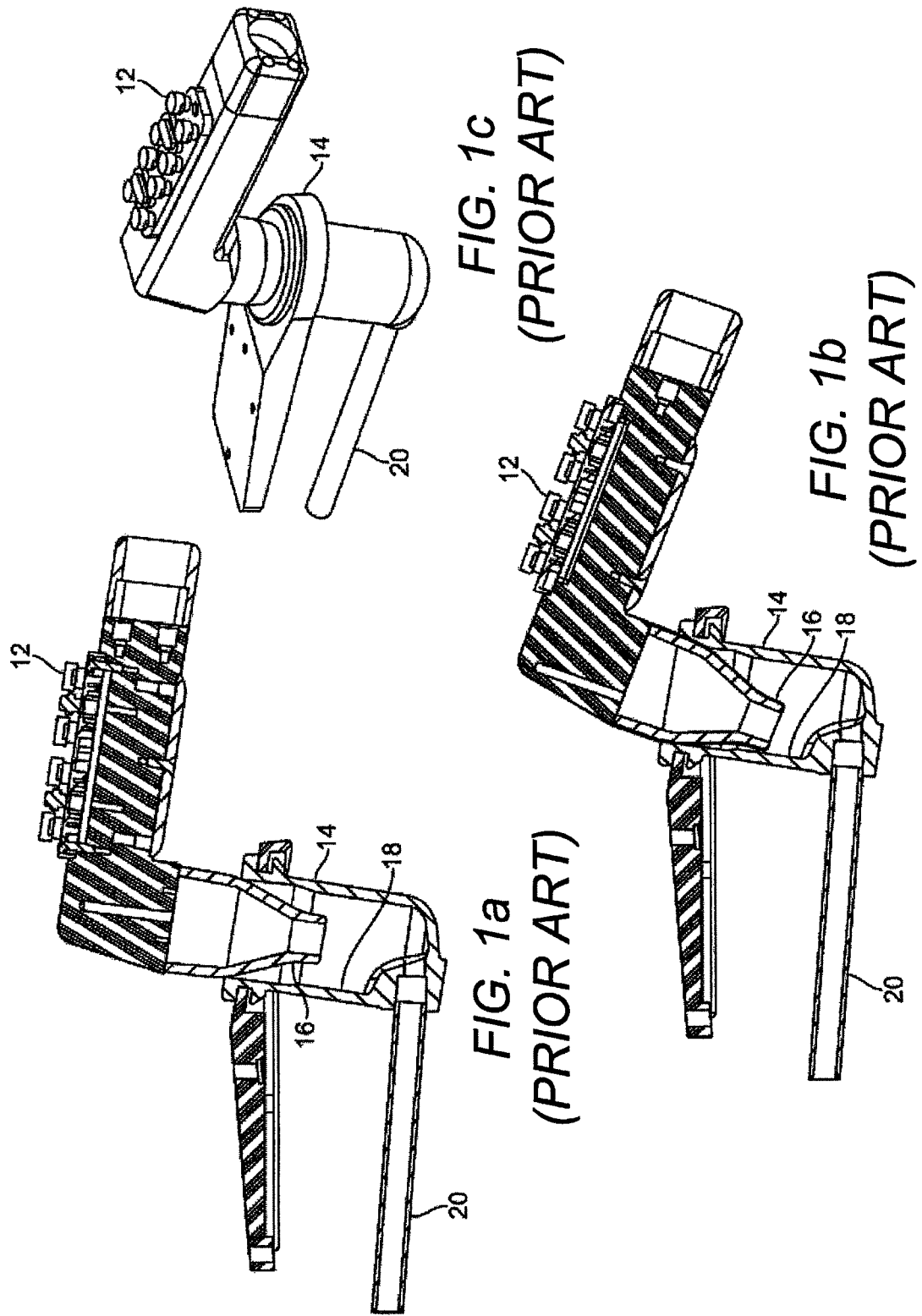

The invention described herein provides methods and means to disinfect dispensing components of food and beverage dispensers. Contained ultraviolet light is applied to the dispensing components to kill molds and/or bacteria on the components. The ultraviolet light can be applied with a sufficient intensity and duration to provide a desired level of disinfection. The ultraviolet light can also be used to generate ozone, which can be used to provide additional disinfection and/or deodorant action, and can be distributed to reach areas of dispensing components not reached by the applied ultraviolet light.

Ultraviolet Disinfection Devices

FIGS. 2a through 2e illustrate a bar gun assembly 100 that includes a bar gun 102 and a holster 104 configured to apply contained ultraviolet light to disinfect dispensing components of the bar gun 102. The holster 104 includes an outer wall 106 that helps to prevent emission of ultraviolet light from the holster 104 during an application of ultraviolet light by the holster 104 onto dispensing components of the bar gun 102 (e.g., nozzle 108).

Figure 2A:
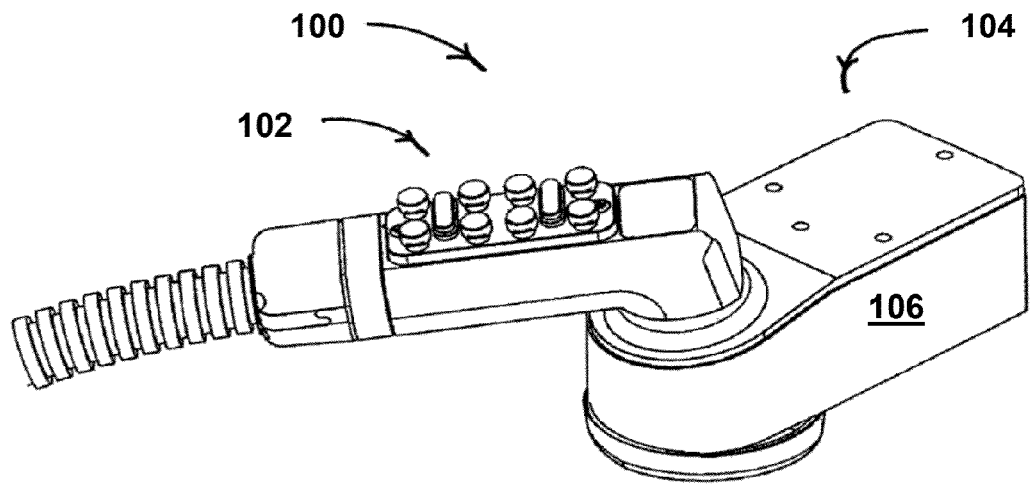
FIGS. 2a through 2e illustrate a bar gun holster configured to apply contained ultraviolet light to disinfect dispensing components of the bar gun, in accordance with an embodiment of the present invention.
Figure 2B:
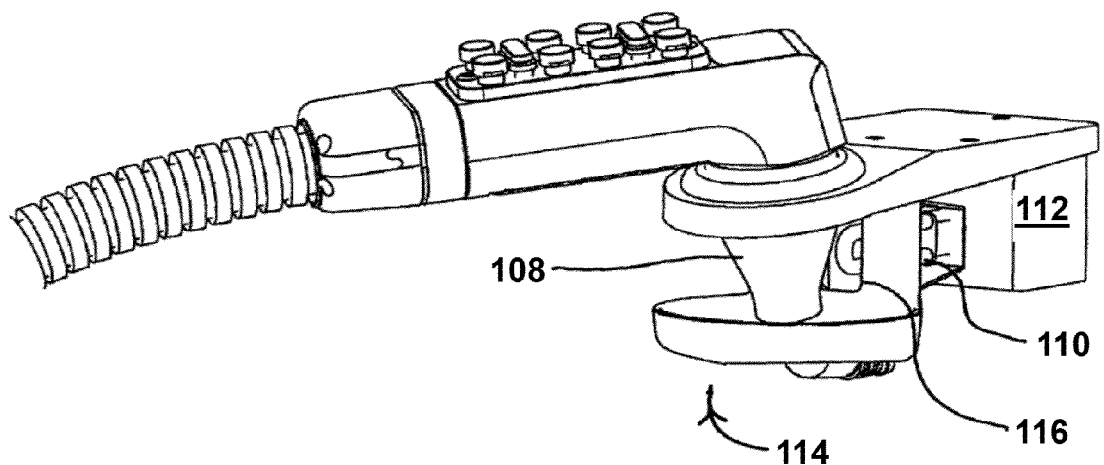
Figure 2C:
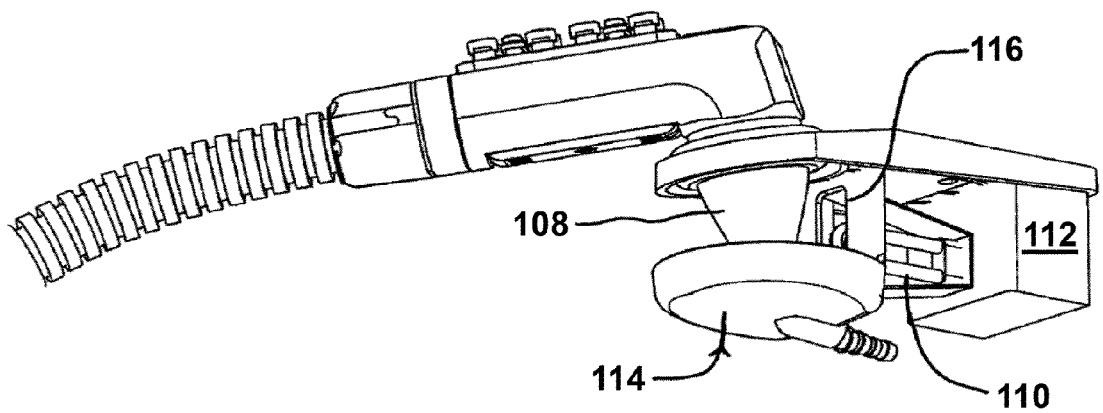
Figure 2D:
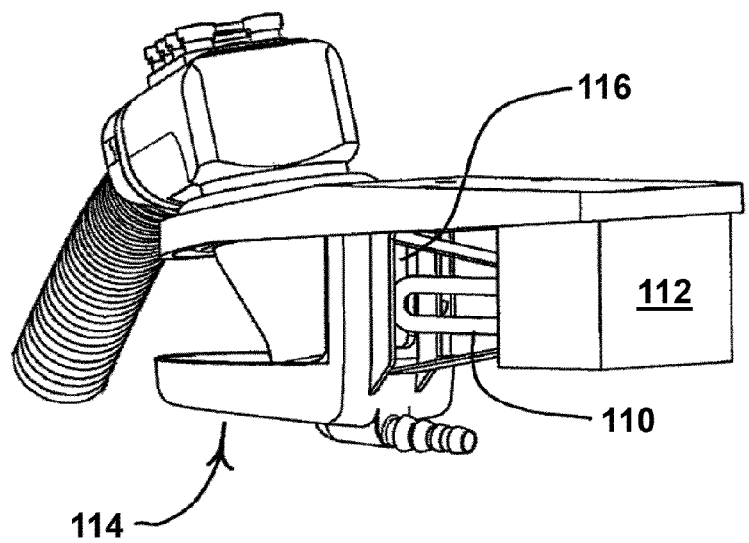

FIG. 2a shows the bar gun 102 stowed in the holster 104. FIGS. 2b through 2d illustrate internal components of the holster 104 (outer wall 106 not shown to avoid obscuring the internal components). The holster 104 includes an ultraviolet light source (e.g., a germicidal lamp or tube lamp 110) mounted in the holster 104 via a lamp mount 112. A germicidal ballast (not shown) for the tube lamp 110 can be mounted within the lamp mount 112. The holster 104 further includes a nozzle receiving portion 114 that accommodates the nozzle 108 when the bar gun 102 is stowed, thereby positioning the nozzle 108 to receive germicidal ultraviolet light emitted by the tube lamp 110. Ultraviolet light emitted by the tube lamp 110 enters the nozzle receiving portion 114 by way of an aperture 116 positioned between the tube lamp and the nozzle receiving portion. One or more inner surfaces of the nozzle receiving portion can be configured (e.g., via a surface finish, an applied surface layer, and via its shape) to reflect ultraviolet light so that ultraviolet light entering through the aperture 116 is reflected onto the nozzle 108 from all sides, including from the bottom so that the ultraviolet light enters into the orifice of the nozzle to at least some extent. For example, the outer wall 106 can be shaped and include an internal reflective surface that evenly distributes the ultraviolet light entering through the aperture 116 to all sides of the nozzle 108.

The holster 104 and/or the bar gun 102 can be configured with a means that senses when the bar gun is stowed in the holster. For example, known switches, contacts, proximity sensors, etc., can be used to sense when the bar gun is stowed. Control circuitry (not shown) can used to activate the tube lamp 110 at suitable times and intervals. The control circuitry can be mounted in a suitable location (e.g., within the lamp mount 112). Although a variable intensity can be used, in many embodiments the ultraviolet light source is configured to emit ultraviolet light at an intensity known to provide a suitable level of disinfection. The control circuitry can keep track of suitable parameters (e.g., time since last ultraviolet application, usage parameters of the bar gun, etc.) to provide periodic applications of ultraviolet light suitable to maintain the nozzle of the bar gun in a disinfected state. In many embodiments, the control circuitry limits the application of ultraviolet light to when the bar gun is stowed and stops any application of ultraviolet light upon removal of the bar gun from the holster. A means to manually initiate the application of ultraviolet light can also be provided (e.g., via a switch, button, control panel interface, etc.).

The holster 104 can also be configured to distribute ozone generated by the ultraviolet light to provide further disinfection and/or deodorant action to dispensing components of the bar gun 102. For example, the holster 104 can further include a circulation means (e.g., a fan) to circulate ozone around the interior of the holster 104 to enhance distribution of ozone around the nozzle 108.

Figure 2E:
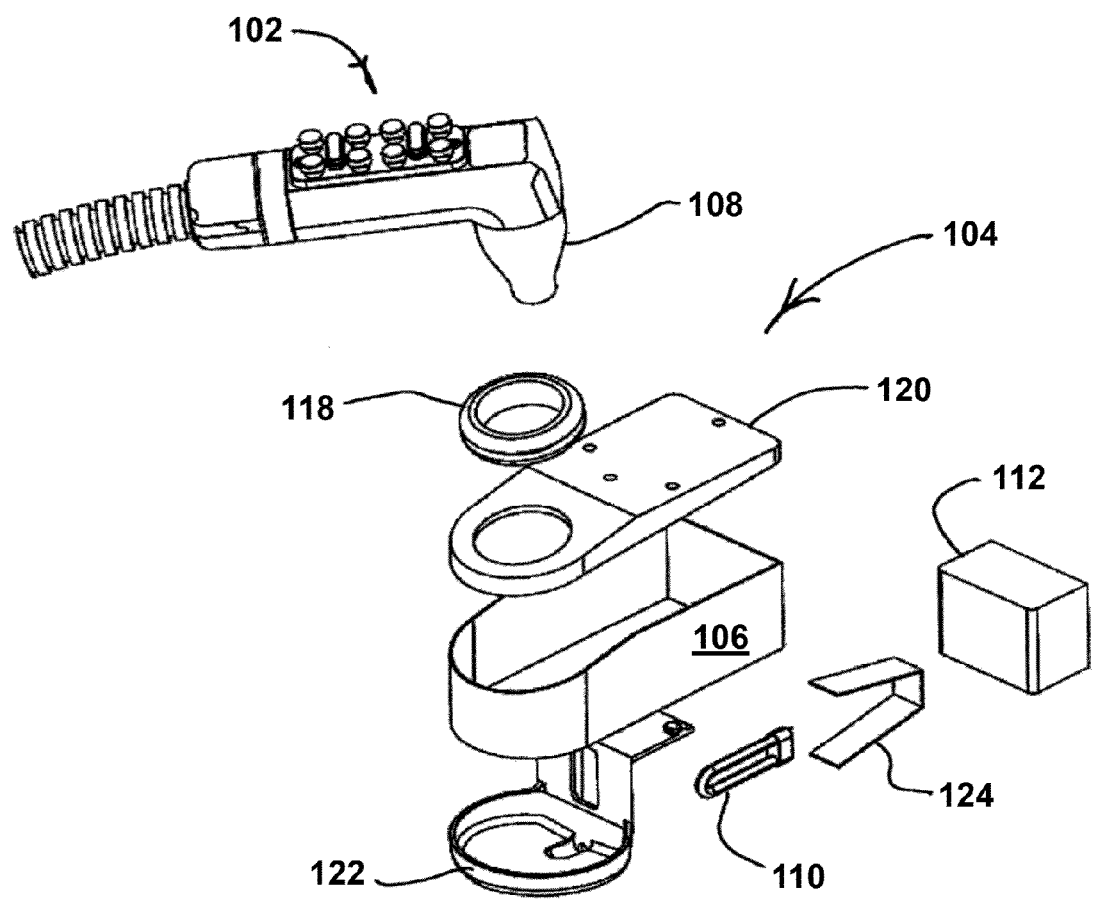

FIG. 2e is an exploded view of the holster 104. The holster 104 includes a grommet 118, a top cover 120, the outer wall 106, a drip collection member 122, the tube lamp 110, a reflector 124, and the lamp mount 112. Components of the holster 104 not shown include the control circuitry for activating the lamp 110, and the above-discussed means for sensing when the bar gun 102 is stowed in the holster. The grommet 118 and the nozzle 108 can be configured with mutually shaped portions to establish and maintain a substantial seal between the nozzle 108 and the grommet 118 when the bar gun is stowed in the holster, thereby preventing the escape of ultraviolet light from the holster and enhancing the concentration of any ozone generated within the holster.

Figures 3A, 3B:
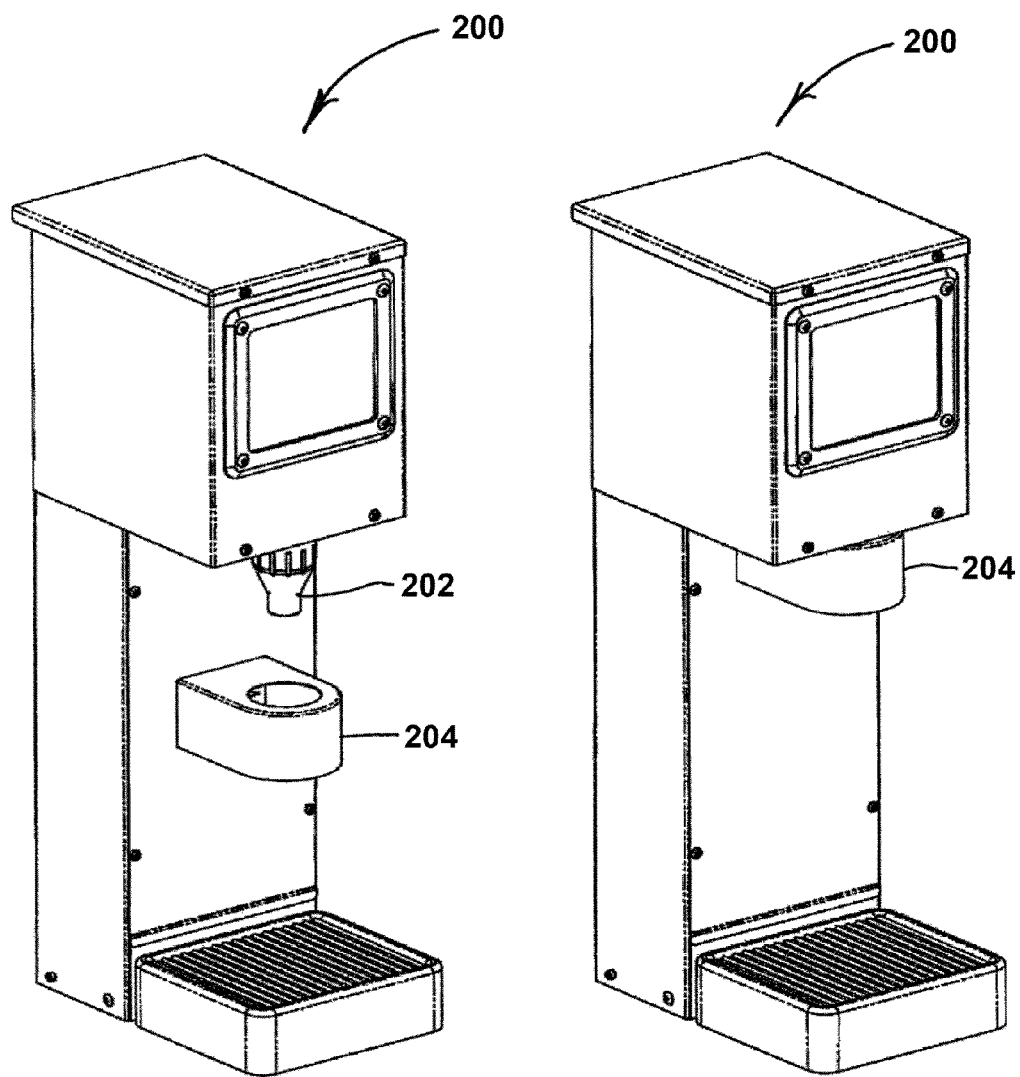
FIGS. 3a and 3b illustrate a beverage dispensing tower configured to apply contained ultraviolet light to disinfect dispensing components of the dispensing tower, in accordance with an embodiment of the present invention.

The above-discussed ultraviolet disinfection can be applied to other types of beverage dispensers. For example, FIGS. 3a and 3b illustrate a beverage dispensing tower 200 configured to periodically apply contained ultraviolet light to disinfect dispensing components (e.g., nozzle 202) of the dispensing tower 200. The beverage dispensing tower 200 includes a disinfecting chamber 204 that is movable to surround the nozzle 202 so that ultraviolet light can be applied to the nozzle 202 in a contained manner. FIG. 3a shows the disinfecting chamber 204 disengaged from the nozzle 202. And FIG. 3b shows the disinfecting chamber 204 positioned to surround the nozzle 202 to contain ultraviolet light during an application of ultraviolet light to the nozzle 202. The ultraviolet light applied can be generated, for example, via an ultraviolet light source mounted within the disinfecting chamber 204, or can be mounted in a suitable location exterior to the disinfecting chamber 204 and the ultraviolet light introduced into the disinfecting chamber (e.g., via an aperture as disclosed above, via one or more fiber optic cables, or via any other suitable known transmission means). Suitable control circuitry, such as discussed above, can be mounted in a suitable location and used to control an actuation of the disinfecting chamber to position the disinfecting chamber and the application of ultraviolet light to provide periodic applications of ultraviolet light, as discussed above with reference to the holster 104.

Figure 4A:
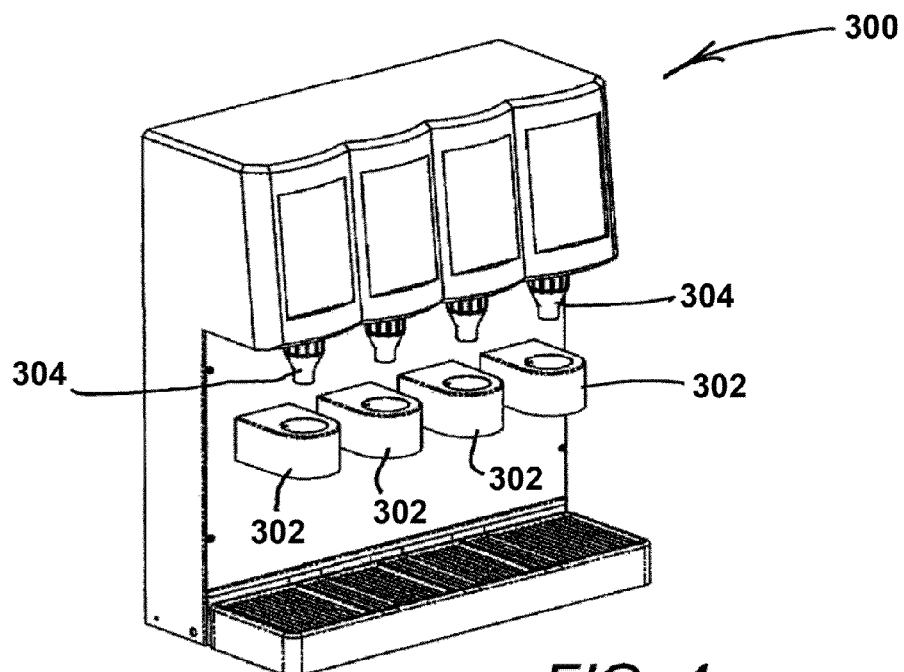
FIGS. 4a and 4b illustrate a multi-nozzle beverage dispensing tower configured to apply contained ultraviolet light to disinfect dispensing components of the multi-nozzle dispensing tower, in accordance with an embodiment of the present invention.
Figure 4B:
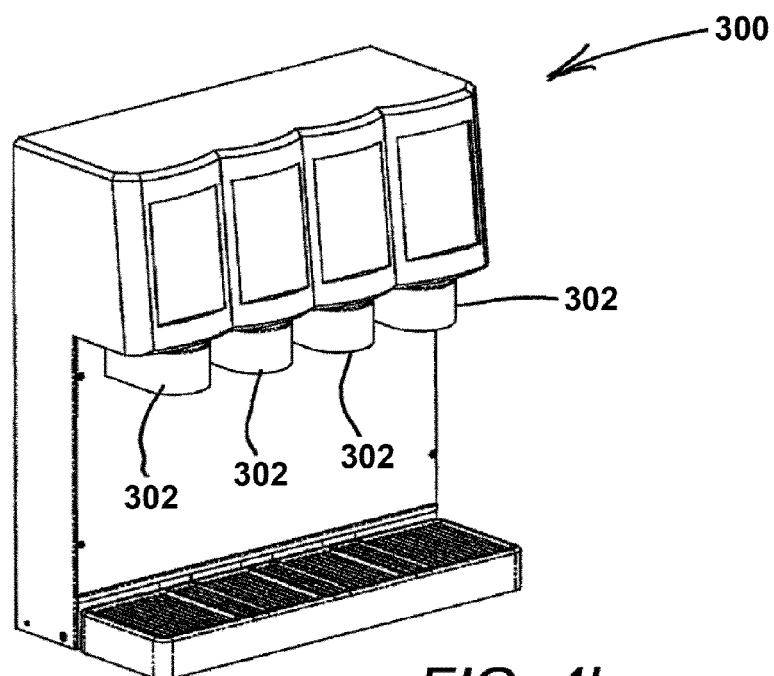

FIGS. 4a and 4b illustrate a similar application of ultraviolet disinfection to a multi-nozzle beverage dispensing tower 300. The multi-nozzle beverage dispensing tower 300 can include multiple disinfecting chambers 302 corresponding to multiple nozzles 304 as illustrated. Alternatively, any number of the disinfecting chambers can be integrated into one or more common disinfecting chambers configured to surround any suitable number of the nozzles during an application of ultraviolet light. The multi-nozzle beverage dispensing tower 300 can include, for example, any of the applicable features and/or functionality discussed above with respect to the holster 104 and the beverage dispensing tower 200.

Figure 5A:
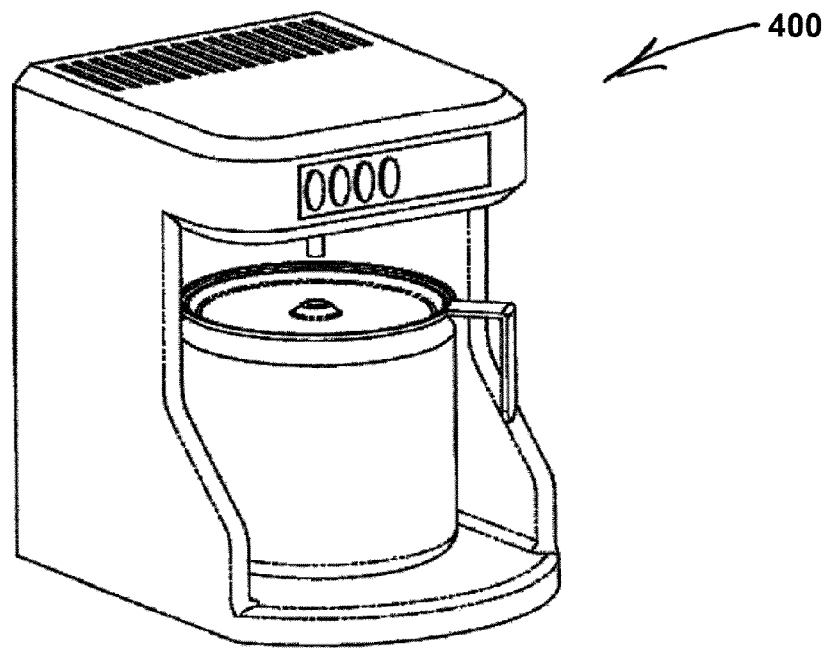
FIGS. 5a and 5b illustrate a coffee maker configured to apply contained ultraviolet light to disinfect dispensing components of the coffee maker, in accordance with an embodiment of the present invention.
Figure 5B:
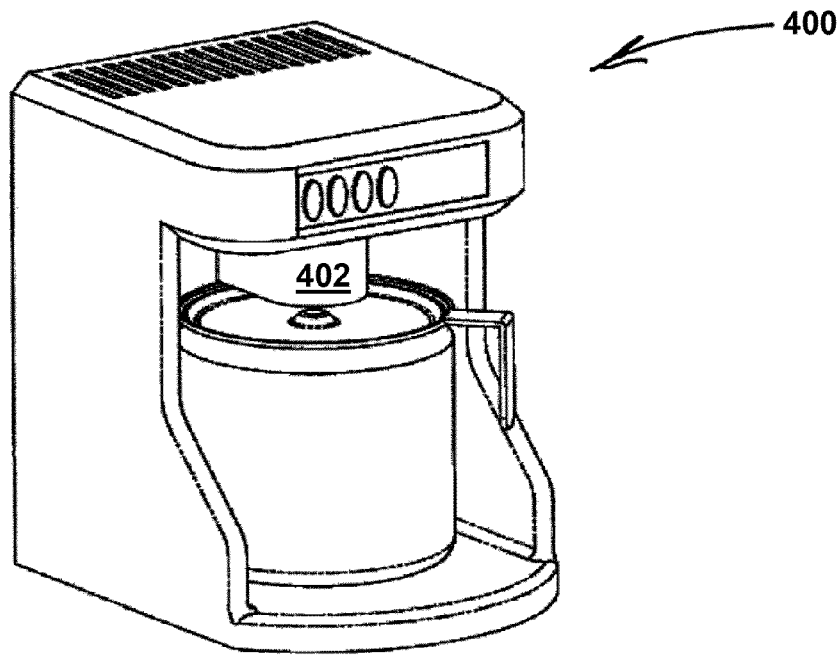

FIGS. 5a and 5b illustrate a coffee maker 400 configured to apply contained ultraviolet light to disinfect dispensing components of the coffee maker 400. The coffee maker 400 includes a disinfecting chamber 402 that can be positioned (e.g., attached, moved, actuated, etc.) for the application of ultraviolet light to dispensing components of the coffee maker 400. The coffee maker 400 can include, for example, any of the applicable features and/or functionality discussed above with respect to the holster 104, the beverage dispensing tower 200, and the multi-nozzle beverage dispensing tower 300.

Figure 6:
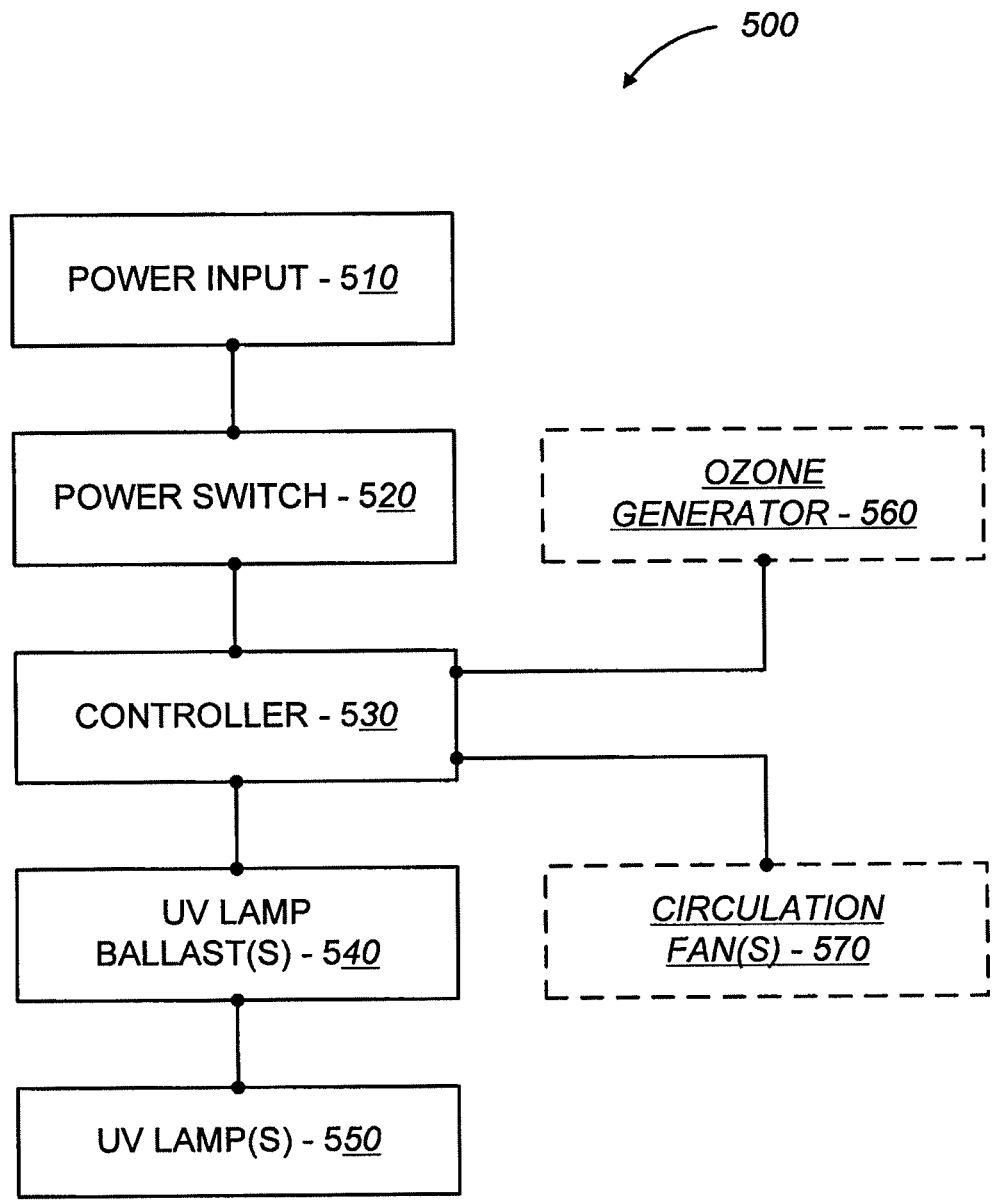
FIG. 6 is a simplified diagram illustrating an ultraviolet light disinfection system, in accordance with an embodiment of the present invention.

FIG. 6 is a simplified diagram illustrating an ultraviolet light disinfection system 500. The disinfection system 500 includes a power input 510, a power switch 520, a controller 530, an ultraviolet lamp ballast(s) 540, and an ultraviolet lamp(s) 550. The disinfection system 500 can also include optional additional components such as an ozone generator 560 and/or a circulation fan(s) 570.

The power input 510 receives electrical power (e.g., alternating current from an external source, direct current from an external source, direct current from an internal battery) used to operate the disinfection system 500. The power input 510 can transfer the received power directly. If required by the operational needs of the disinfection system, the power input can also convert the received power into one or more forms used by components of the disinfection system (e.g., into a DC voltage suitable to operate digital circuitry in the controller; into any form required to operate the lamp ballast(s) 540, the lamp(s) 550, the ozone generator 560, and/or the circulation fan(s) 570). In many embodiments, the power switch is an on/off switch used to activate and deactivate the disinfection system.

In many embodiments, the controller 530 is configured to periodically activate the UV lamp(s) 550 to maintain a food or beverage dispenser in a disinfected state. For example, the controller can include an interval timer that provides a periodic application of power to the lamp ballast(s) 540. The controller can be implemented in any suitable manner (e.g., using analogue components, using digital components, a mix of analogue and digital components). The controller can also be programmable through, for example, a suitable user interface and/or communication channel.

While the above-discussed embodiments involve certain types of beverage dispensers, the present invention is not limited to such beverage dispensers. For example, contained ultraviolet light can be applied to other types of beverage dispensers and/or food dispensers. Such food dispensers include, for example, a hot cheese dispenser (e.g., as described in U.S. Patent Publication No. 2009-023544 A1, the entire disclosure of which is incorporated herein by reference); a refrigerated milk dispenser (e.g., as described in U.S. Pat. No. 6,832,487, the entire disclosure of which in incorporated herein by reference); a pizza sauce dispenser (e.g., as described in U.S. Pat. No. 7,074,277, the entire disclosure of which is incorporated herein by reference); and a liquid egg dispenser (e.g., as described in U.S. patent application Ser. No. 11/763,992, the entire disclosure of which is incorporated herein by reference).

Figure 7:
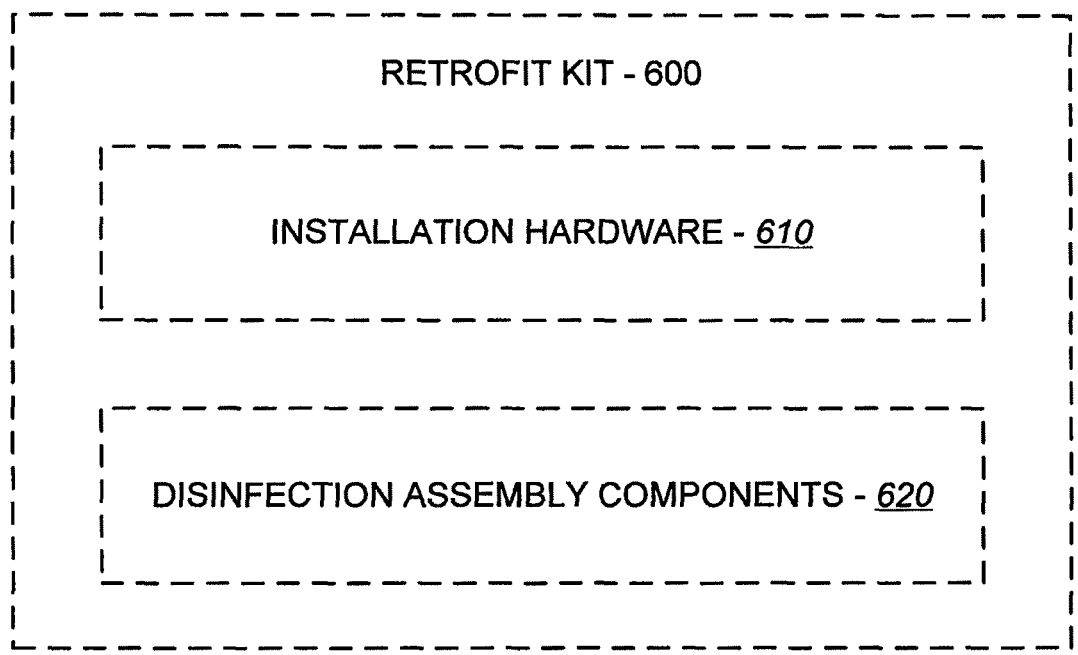
FIG. 7 is a simplified diagram illustrating a retrofit kit for retrofitting an ultraviolet light disinfection system to a pre-existing food or beverage dispenser, in accordance with an embodiment of the present invention.

The disclosed disinfection devices and system can also be retrofitted to existing food or beverage dispensers. FIG. 7 is a simplified top-level diagram illustrating a retrofit kit 600 for retrofitting an ultraviolet light disinfection system to a pre-existing food or beverage dispenser. The retrofit kit 600 includes installation hardware 610 and disinfection assembly components 620. In many embodiments, the disinfection assembly components 620 include, for example, one or more ultraviolet light sources such as the UV lamp(s) 550, a housing/shield component(s) used to contain the ultraviolet light, and related electrical components such as the power input 510, the power switch 520, the controller 530, the UV lamp ballast(s) 540, and any related electrical connecters/wires. A variety of retrofit kits can be configured for use on a wide variety of existing food and beverage dispensers. Each retrofit kit can be configured for use on one or more existing food and/or beverage dispenser types/models.

As will be understood by those skilled in the art, the present invention may be embodied in other specific forms without departing from the essential characteristics thereof. These other embodiments are intended to be included within the scope of the present invention, which is set forth in the following claims.

What is claimed is:

1. An apparatus for disinfecting a nozzle of a beverage dispensing handle, the apparatus comprising:
a drip collection member, comprising:
a base;
a dividing wall extending upward from the base; and,
a mounting plate that extends transverse from the dividing wall, the dividing wall having an aperture and the base having a drain;
a lamp mount;
an outer wall installed over and around the drip collection member to adjoin the base and encase the dividing wall, such that the outer wall, base of the drip collection member, and a first side of the dividing wall define a first chamber for enclosing the nozzle of the beverage dispensing handle when the nozzle is inserted into the first chamber, and the outer wall, lamp mount and a second side of the dividing wall define a second chamber;
a cover coupled to the mounting plate of the drip collection member and further defining the first and second chambers, the cover having a nozzle opening aligned with the first chamber and configured to hold the nozzle of the beverage dispensing handle such that only the nozzle extends into the first chamber; and,
an ultraviolet light generator installed within the second chamber, the ultraviolet light generator being separated from the first chamber by the dividing wall, the ultraviolet light generator configured to generate and emit germicidal ultraviolet light through the aperture and into the first chamber,
wherein, when assembled, the mounting plate attaches to an underside of the cover, the underside being the side defining the first and second chambers,
wherein the aperture connects an interior of the first chamber with an interior of the second chamber.

2. The apparatus of claim 1, wherein the cover is configured to hold the nozzle such that the beverage dispensing handle extends from the apparatus in cantilever.

3. The apparatus of claim 2, wherein the first chamber substantially contains the ultraviolet light within the first chamber.

4. The apparatus of claim 3, wherein the outer wall further comprises reflective internal surfaces configured to reflect the ultraviolet light onto the nozzle.

5. The apparatus of claim 4, wherein the drip collection member further comprises a reflective internal bottom surface configured to reflect the ultraviolet light onto the nozzle.

6. The apparatus of claim 5, wherein the reflective internal surfaces are shaped to distribute the ultraviolet light within the first chamber.

7. The apparatus of claim 6, further comprising a reflector partially surrounding the ultraviolet light generator to direct ultraviolet light through the aperture.

8. The apparatus of claim 1, further comprising a controller configured to intermittently activate the ultraviolet light generator to maintain the nozzle in a disinfected state.

9. The apparatus of claim 8, wherein the controller provides for a manually-initiated application of ultraviolet light.

10. The apparatus of claim 1 wherein the cover further comprises a grommet installed in the nozzle opening and configured to mate with the nozzle for sealing the first chamber closed to prevent escape of ultraviolet light from the first chamber when the beverage dispensing handle is installed in the nozzle opening.

* * * * *